US007352469B2

(12) United States Patent
McGrew

(10) Patent No.: US 7,352,469 B2
(45) Date of Patent: *Apr. 1, 2008

(54) QUANTUM RESONANCE ANALYTICAL INSTRUMENT

(76) Inventor: Stephen P. McGrew, 9715 W. Sunset Hwy., Spokane, WA (US) 99224

( * ) Notice: Subject to any disclaimer, the term of this patent is extended or adjusted under 35 U.S.C. 154(b) by 461 days.

This patent is subject to a terminal disclaimer.

(21) Appl. No.: 11/041,005

(22) Filed: Jan. 19, 2005

(65) Prior Publication Data

US 2005/0185188 A1  Aug. 25, 2005

Related U.S. Application Data

(63) Continuation-in-part of application No. 10/286,338, filed on Nov. 1, 2002, now Pat. No. 6,930,779.

(60) Provisional application No. 60/338,506, filed on Nov. 6, 2001.

(51) Int. Cl.
*G01B 9/02* (2006.01)
*G01B 11/02* (2006.01)
*G01J 3/45* (2006.01)
*G01J 3/44* (2006.01)

(52) U.S. Cl. .................... 356/451; 356/301; 356/491

(58) Field of Classification Search ............. 356/450, 356/451, 491, 495, 301, 326
See application file for complete search history.

(56) References Cited

U.S. PATENT DOCUMENTS

| | | | |
|---|---|---|---|
| 5,530,544 | A | 6/1996 | Trebino et al. |
| 5,541,947 | A | 7/1996 | Mourou et al. |
| 5,589,936 | A * | 12/1996 | Uchikawa et al. ......... 356/450 |
| 5,818,583 | A * | 10/1998 | Sevick-Muraca et al. ... 356/336 |
| 6,181,419 | B1 * | 1/2001 | Snelling et al. ............. 356/336 |
| 6,201,916 | B1 | 3/2001 | Eggleton et al. |
| 6,219,142 | B1 | 4/2001 | Kane |
| 6,456,380 | B1 | 9/2002 | Naganuma |

(Continued)

OTHER PUBLICATIONS

"Feedback Quantum Control of Population Transfer Using Shaped Femtosecond Pulses," C.J. Bardeen, V.V Yakovlev, K.R. Wilson, S.D. Carpenter, P.M. Weber and W.S. Warren in *Ultrafast Phenomena XI*, 1998, pp. 465-467.

*Primary Examiner*—Patrick Connolly
(74) *Attorney, Agent, or Firm*—Dorsey & Whitney LLP

(57) ABSTRACT

Quantum resonance fluorescent microscope systems for detecting component substances in a specimen are described. The systems are based on exciting the sample containing the material with a femtosecond to nanosecond probe pulse of collimated light, which is tailored to optimize detection of a given material by separating the probe pulse into component features of frequency, polarization, phase and/or amplitude. The component features are independently shaped and formed into a composite pulse selected to optimize a signature response pulse received from the material. In some cases, two independently re-shaped pulses are combined, where one re-shaped pulse has two mixed polarization states and the other re-shaped pulse is linearly polarized. These two pulses are made to intersect at an angle of 90 degrees so that the combined pulse has electric field in each of the XYZ axes. Selection of the appropriate shapes for the component features of the pulses for a given material is accomplished by testing variations in the features on the material, assigning a fitness value to variants that tend to optimize a distinctive spectral response from the material, and using a genetic algorithm to select the combination of component features that enhances the distinctiveness of the response received over a typical background.

20 Claims, 8 Drawing Sheets

U.S. PATENT DOCUMENTS 6,930,779 B2 *  8/2005  McGrew ..................... 356/451
7,187,441 B1 *  3/2007  Sevick-Muraca et al. ... 356/336

2004/0085540 A1 *  5/2004  Lapotko et al. ............. 356/432
2004/0128081 A1    7/2004  Rabitz et al.

* cited by examiner original pulse          shaped pulse

QUANTUM RESONANCE ANALYTICAL INSTRUMENT

CROSS-REFERENCE TO RELATED APPLICATION

This application is a Continuation-in-Part of pending U.S. patent application No. 10/286,338, filed Nov. 1, 2002, now U.S. Pat. No. 6,930,779 which claims the benefit of Provisional Patent Application No. 60/338,506, filed Nov. 6, 2001.

TECHNICAL FIELD

The invention relates to methods and devices for detecting materials in a sample by separating a coherent radiation pulse directed onto the sample into a plurality of pulses of different polarization sates, modulating the amplitude or phases of the separate pulses and coherently recombining the pulses into a composite pulse having component features selected by an evolutionary algorithm to distinguish the materials in the sample via the material's spectral response.

BACKGROUND OF THE INVENTION

Prior art includes a large body of published work relating to the shaping of femtosecond pulses and the interactions between various materials or molecules with the shaped pulses. It has been observed that in nonlinear systems such as molecules and semiconductor materials, intense light pulses of certain shapes can be used to enhance the fluorescent emission at particular wavelengths. The specific pulse shape needed depends on the complex energy band structure of the molecules or materials being studied. In principle, a detailed and precise understanding of the physics involved should be enough to calculate the optimal pulse shape, but in practice our understanding is insufficient and our computational tools are too crude to do the calculations.

In "Feedback quantum control of population transfer using shaped femtosecond pulses", published in *Ultrafast Phenomena XI*, 1998, K. R. Wilson and his associates demonstrated a method for evolving an optimal pulse shape to control the quantum state of a complex molecular system. The method is illustrated in FIG. 1. A very brief light pulse is spread into a spectrum by a diffraction grating, then the spectrum is passed through a spatial light modulator that modulates each spectral component independently. The modulator can operate on phase, amplitude or both. Typical spatial light modulators used for pulse shaping are acousto-optic modulators, liquid crystal modulators and deformable-mirror arrays. The pulse is then reconstituted by focusing the modulated spectral components back to a point on a diffraction grating, which combines the components coherently into a single pulse. In essence, the spatial light modulator acts on the temporal Fourier transform of the initial pulse to re-form it in any way desired.

A substance such as a particular protein responds nonlinearly to a pulse of light. For example, an ultraviolet light pulse a few tens of femtoseconds long will induce fluorescence in most substances; and the spectrum of the fluorescence depends on the intensity of the pulse. If the intensity is great enough, there is an increased probability of multiphoton absorption resulting in electrons being elevated to energy levels higher than the energy of a single photon, which leads to emission at wavelengths that single-photon absorption cannot produce.

In addition to intensity, the spectral content of a light pulse and the relative phase and polarization of the spectral components can affect strongly the response of an illuminated sample. For example, it has been shown by Bardeen et al (Ref. 1) that when a laser light pulse is shaped appropriately, the intensity of a fluorescence emission line from an irradiated sample can be much higher than it is with an arbitrarily shaped pulse. That is, the ratio of the intensity of a specific emission line to the intensity of another specific emission line can be maximized by using an optimally-shaped pulse.

The importance of pulse shape to the response of a nonlinear system like an atom can be understood by considering a double pendulum stimulated by a short series of impacts. If a series of impacts strike the pendulum at times separated by a time equal to the period of the fundamental mode of the pendulum, the pendulum will respond by swinging without wiggling. If, however, the impacts are timed so that some are synchronous with the fundamental mode, but other impacts are interspersed with the first impacts so that the other impacts are synchronous with the vibrational period of the upper mass, the pendulum will respond by both swinging and wiggling. In the case of a quantum mechanical system like a molecule, a properly shaped pulse can elevate electrons to a specific energy level and then give them a second "kick" to elevate them further to another energy level that is otherwise not easily accessible. Decay from that energy level to other energy levels en route to the ground state, then, produces emission lines that will only be present when the excitation pulse has precisely the shape required to provide the first "kick" followed by a properly timed second "kick". Furthermore, the direction of the electric fields in a pulse during the first and second "kicks" is important because the vibratory state or quantum state of an electron in a molecule or atom has a directional component. So, in an optimal pulse, the polarization state of the light may need to change once or even several times within the pulse duration in order to elevate the illuminated substance to a desired quantum state.

In the prior art, femtosecond laser pulses have been shaped by forming their temporal Fourier transform, manipulating individual Fourier components independently in both phase and amplitude, and then forming the inverse Fourier transform. This is accomplished as illustrated in FIG. 1, by forming the dispersed spectrum of an original pulse 153 using a diffraction grating 130, passing the spread spectrum through a spatial light modulator 105, 110 (such as a liquid crystal light valve or an acousto-optic light modulator) to selectively attenuate and/or delay various portions of the spectrum, and then focusing the spectrum back together onto a second diffraction grating 100, where the pulse is re-formed, producing a pulse having a modified shape.

Also in the prior art, the optimum pulse shape is determined empirically by monitoring the emission spectrum of a sample irradiated by the shaped pulse and adjusting the shape until the emission spectrum is optimized. For example, if the spatial light modulator 105, 110 is a liquid crystal light modulator, the pixels of the modulator can be treated as "genes" while the height of a specific emission line can be treated as "fitness" in a genetic algorithm or other evolutionary algorithm.

The basic techniques of laser pulse shaping and pulse shape optimization have been explored by many researchers, with the purpose of performing measurements on molecular dynamics, generating x-rays, and controlling chemical reactions.

SUMMARY OF THE INVENTION

Disclosed herein are an apparatus and method for recognizing specific molecules, complexes or other substances or structures by subjecting a sample to a query pulse and detecting a response pulse. The query pulse is tailored to the specific substance or structure, and the response pulse produced by a substance or structure in response to the query pulse is unique to the substance or structure being sought. X-ray, UV, visible, IR, terahertz, RF, or acoustic pulses are used as appropriate for the substance or structure being sought. The response pulse may be X-ray, UV, visible, IR, terahertz, RF, or acoustic; and is not necessarily the same type as the query pulse. A unique feature of the present invention is the use of query pulses tailored in the amplitude and phase of spectral content in order to stimulate optimally a specific response that is specific to the substance or structure being sought.

BRIEF DESCRIPTION OF THE INVENTION

The present invention employs shaped pulses to recognize specific substances and structures. Whereas prior art has used shaped pulses to study the quantum dynamics of specific molecules, there is no prior art in which shaped pulses have been used to recognize, identify or detect specific molecules or substances.

According to the present invention, a short coherent pulse of radiation is shaped by selectively attenuating and/or delaying various spectral and/or polarization components of an original pulse. The shaped pulse is focused onto a substance. The pulse interacts nonlinearly with the substance to produce a characteristic response if the pulse shape is precisely tailored to the structure of the substance. Other substances with different structures do not produce the same response to pulses of that particular shape. When the characteristic response is received from a sample irradiated with that particular pulse shape, it is then known with very high confidence that the sample contains the corresponding substance.

Figure 1:
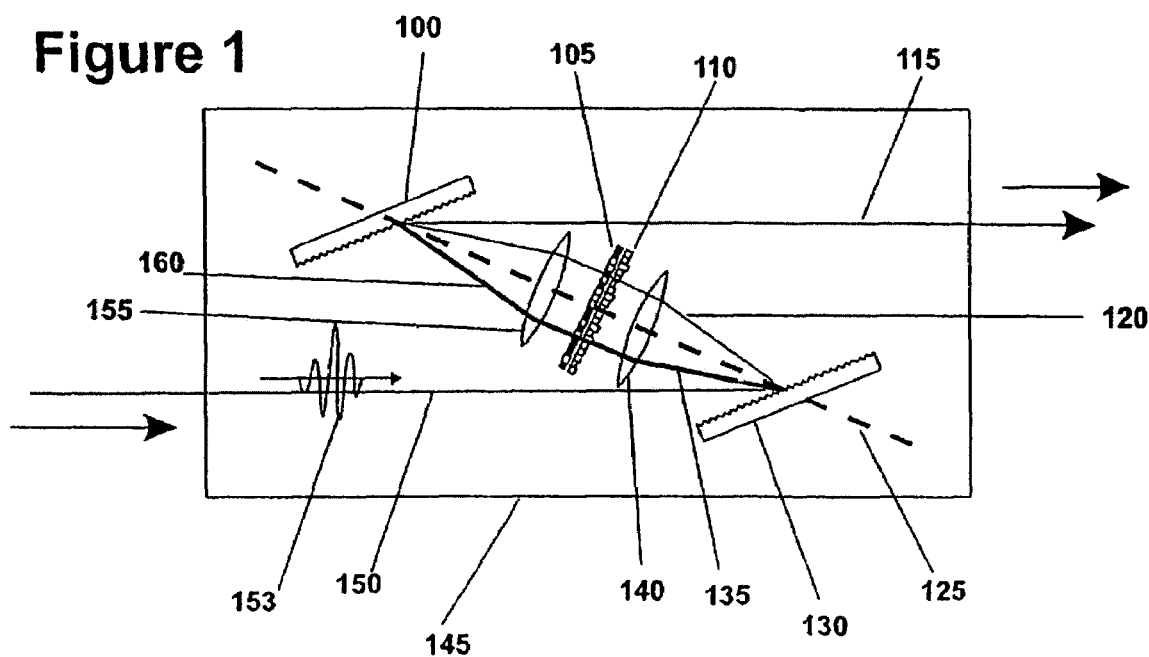
FIG. 1 illustrates a pulse shaper using a combination of prior art methods for shaping femtosecond light pulses adaptively.
Figure 5:
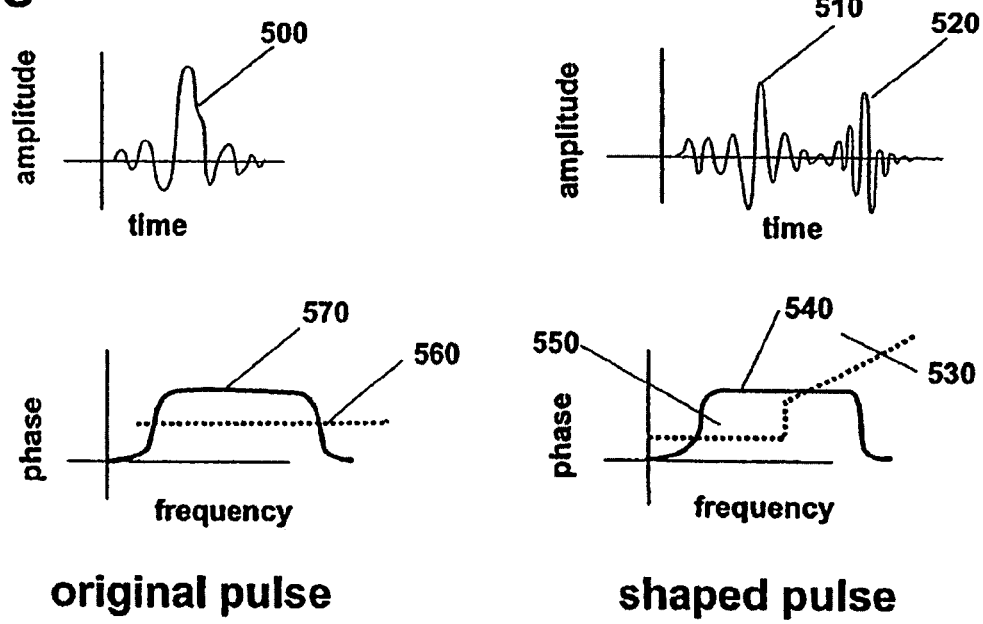
FIG. 5 illustrates various representations of an optical pulse before and after pulse shaping in phase and amplitude only.

As described in prior art publications and illustrated in FIG. 5 (original pulse), a femtosecond laser pulse contains a broad continuum of light frequencies. The pulse may be spectrally dispersed by focusing it to a narrow beam and reflecting it from a diffraction grating as illustrated in FIG. 1. As shown in FIG. 1, the spread spectrum is then passed through a spatial light modulator such as an acousto-optic modulator or a liquid crystal TV screen, or it may be reflected from a deformable-membrane spatial light modulator or an equivalent reflective modulator. The spatial light modulator selectively delays and/or attenuates the various spectral components of the pulse. The spectrum emerging from the modulator is then refocused to a point and reflected again from a diffraction grating to re-form the pulse. The re-formed pulse has a new shape depending on the details of the modulation performed on the various spectral components. FIG. 5 illustrates an original pulse 500 re-shaped into a new pulse that has a low-frequency component 510 that is slightly delayed relative to a higher-frequency component 520. The re-shaping in this case is accomplished by spreading the original pulse into a spectrum 570, then delaying the phase of the lower-frequency components 500 of the spectrum. Note that in the case illustrated in FIG. 5, the relative phase delay is proportional to the frequency, but in general any phase delay versus frequency relationship may be used.

In the present methods, the shaped pulse is used to excite fluorescence from a known substance; and an optimization procedure is followed to discover a particular modulation function that maximally enhances a distinctive spectral feature in the fluorescence spectrum emitted by the substance. For example, a single emission line having relatively low intensity in the ordinary fluorescence spectrum might be enhanced by one or more orders of magnitude by an excitation pulse having an optimal shape. Alternatively, one emission line or other feature that is ordinarily in the fluorescence spectrum might be greatly decreased when the excitation pulse has a specific shape, or, a combination of features in the absorption spectrum may be enhanced or diminished by exciting the substance with an optimal pulse. The spectral features of interest may be measured at the time of the excitatory pulse, or at any time thereafter. The absorption spectrum and emission spectrum of a substance are dependent on the quantum state of a substance, and the quantum state typically changes very rapidly following initial excitation. Accordingly, it is advantageous to employ two or more pulses. The first pulse may be called a "pump" pulse, and subsequent pulses may be called a "probe" pulse.

Sometimes it is advantageous to illuminate the sample first with a long-duration coherent pulse up to several milliseconds long, to place most of the target molecules in the sample into a specific first quantum state. Then a second, brief shaped pulse may be used to move the target molecules from the first quantum state to a second quantum state; and finally a third, brief shaped pulse may be used to measure the number of molecules in the second quantum state via a measurement of the absorption spectrum or the emission spectrum. The relative timing and phase of the pump and probe pulses can affect the response of the molecules to the pulses dramatically.

It is not within the current capabilities of the art to predict exactly what pulse shape is needed to enhance or decrease a given feature of the fluorescence spectrum of a particular substance. However, a pulse-shaping system may be "trained" to generate a pulse shape that has the desired effect, as described by Bardeen et al (Ref. 1). If necessary, the pulse shape can then be calculated from the modulation applied to obtain the effective pulse, or the pulse shape can be measured directly. In the present invention it is not necessary to know the pulse shape; it is only necessary to discover the control parameters for the pulse shapers needed to generate a pulse that produces a characteristic response from a target substance.

Figure 3:
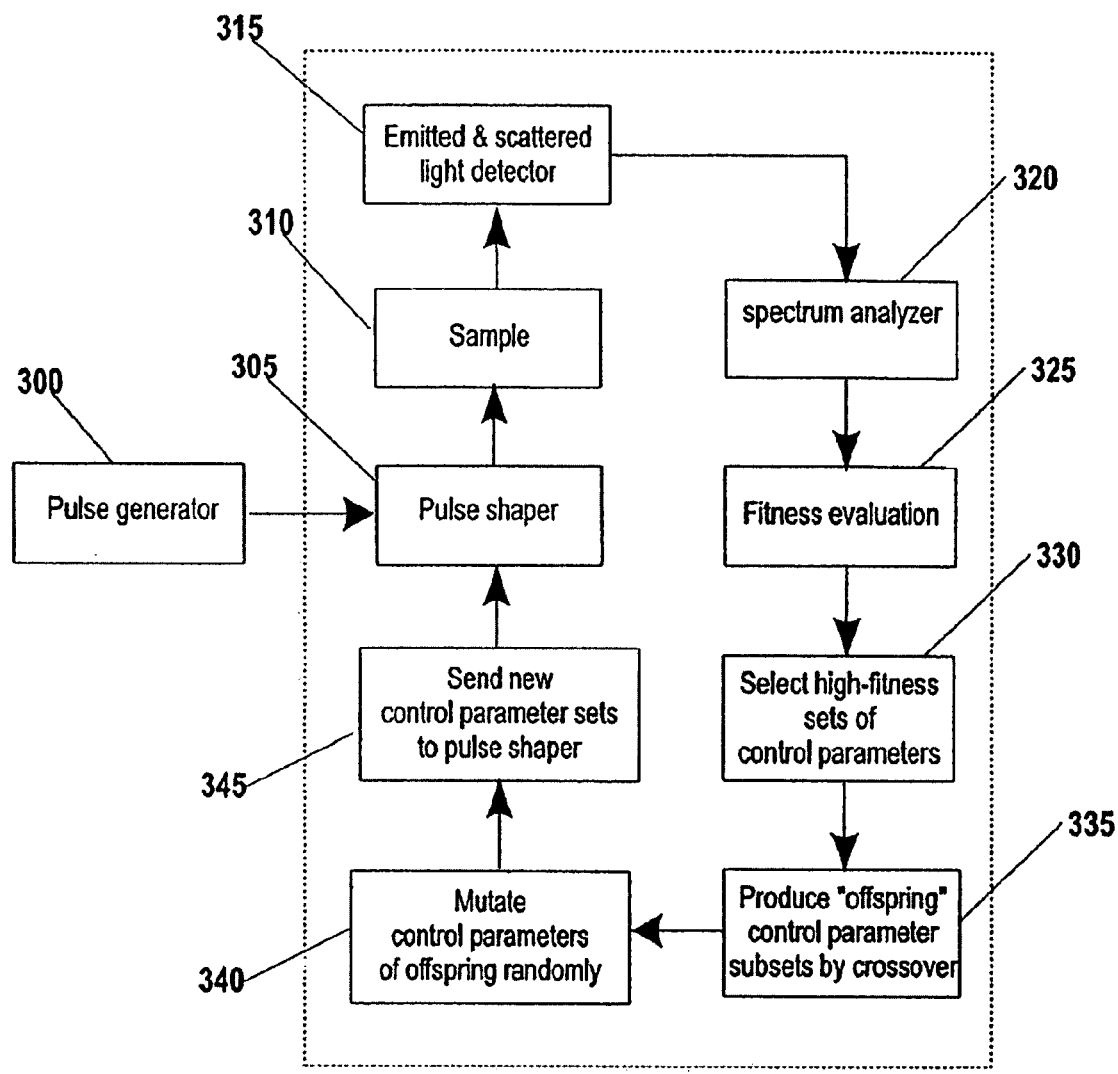
FIG. 3 is a diagram representing the training procedure for recognition of a specific substance.

A procedure for carrying out the processes involved in this invention according to an evolutionary algorithm is diagrammed in FIG. 3. A light pulse generator 300 emits a stream of pulses of consistent shape and structure. A pulse shaper 305 adjusts the shape of each light pulse, which is conveyed to a sample 310. Emitted and scattered light is detected by detector 315, and its spectrum is analyzed by a spectrum analyzer 320. The "fitness" of the pulse shape is determined by a fitness evaluator 325. Fitness may be, for example, the inverse of the integral of the square of the difference between the normalized intensities of corresponding spectral components of the emission or absorption spectrum from the sample in response to an un-shaped pulse and the shaped pulse. In that case, the pulse shape is optimum when the fitness is maximized.

A "population" of different pulse shapes are generated by the pulse shaper, and the fitness of each pulse shape in the population is calculated. The high-fitness pulses (that is, the control parameter sets that determine the shapes of the pulses) are selected 330 to produce "offspring" sets of control parameters to determine new pulse shapes in a subsequent generation. The "offspring" may be constructed 335 by the evolutionary operators of recombination or mutation 340, or by a mixture of the two operations of an evolutionary algorithm. The offspring are sent 345 to the pulse shaper to complete the first cycle. A nearly optimum pulse shape is achieved after a series of such cycles.

If a particular spectral feature and an optimal pulse shape have been found for a given substance, then that pulse shape and the spectral feature together are unique to that substance.

It is a primary objective of the methods disclosed herein to use an optimally shaped laser pulse as a probe to excite light emission from an unknown sample, and to determine the presence of an absence of a known substance in that sample by the presence or absence of the corresponding spectral feature in the emission.

Another purpose of the methods disclosed herein is to provide a new way to identify specific substances by observing their optical response to laser pulses whose shapes are tailored to produce a specific optical response in specific substances.

Another purpose of the methods disclosed herein is to provide a system that rapidly detects specific pathogens or chemical/biological warfare agents.

Another purpose of the methods disclosed herein is to identify documents, products or packages by detecting the relative quantities of specific substances on those items.

Another purpose of the methods disclosed herein is to identify and measure the quantity of specific molecular species in fluids or gasses.

Another purpose of the methods disclosed herein is to provide a scanning near-field optical microscope capable of detecting, identifying and locating specific molecular species or elements in a sample with nanometer-scale resolution.

Another purpose of the methods disclosed herein is to provide an apparatus for controlling the three-dimensional temporal structure of an optical pulse during the time evolution of the pulse.

Another purpose of the methods disclosed herein is to provide a method for obtaining a unique "signature" for a molecular species.

Another purpose of the methods disclosed herein is to sort molecules, microbes, cells, spores and other particles by their optical properties.

Another purpose of the methods disclosed herein is to selectively kill specific microbial or cellular species in a sample by irradiating the sample with pulses that interact selectively with those species.

Another purpose of the methods and apparatus disclosed herein is to selectively affect cell components containing molecules of specific types.

Another purpose of the methods disclosed herein is to extend the capabilities of NMR spectroscopy.

Another purpose of the methods disclosed herein is to provide a general method for excitation of specific vibrational modes in nonlinear structures by use of a shaped pulse of acoustic, optical, RF or other radiation.

Another purpose of the methods disclosed herein is to provide a method for driving a population of molecules into a predetermined quantum state, as opposed to driving only certain atoms in the molecules into a predetermined quantum state.

Beyond the purposes and objectives described above, the methods disclosed herein have useful applications in rapid screening of mail for pathogens, detection of pathogens in water, rapid counting and identification of fluorophore-tagged microbes, viruses and molecules, stimulation and control of specific chemical reactions, control of quantum states in nanometer-scale semiconductor "quantum dots", manipulating quantum states of molecules and quantum-mechanical structures for quantum computation, and optimizing any process involving the interaction of light with matter. When the pulsed radiation is x-rays rather than visible light, optimization of the shape of a pulse improves contrast of x-ray imaging by enhancing the absorption of x-rays by specific substances.

DETAILED DESCRIPTION

Embodiment #1

Apparatus and Method for Detecting Anthrax Spores or Other Pathogens

Figure 12:
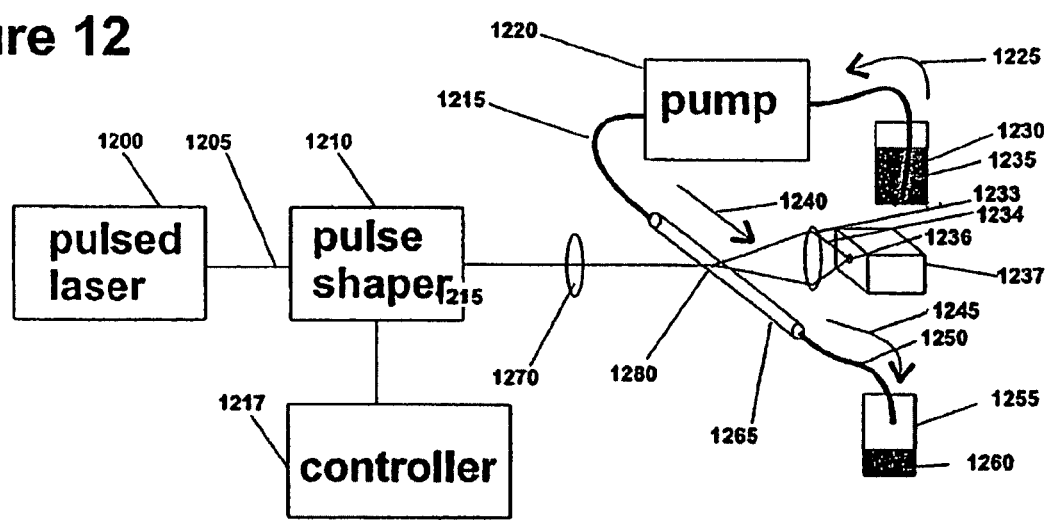
FIG. 12 illustrates an apparatus for selectively killing specific cells or spores via shaped optical pulses.

The apparatus of FIG. 12 includes a source 1200 of femtosecond light pulses, a pulse shaper 1210, a fluorescence spectrometer 1237, optics 1270 to direct shaped light pulses to a sample of fluid in a sample holder 1265, means 1237 for analyzing the spectrum and polarization of light emitted by the sample in response to illumination by a light pulse, and means 1217 for controlling the pulse shaper 1210. In the example shown in FIG. 12, the sample holder is a transparent capillary tube 1265, a source reservoir 1230, the tubing 1215 and 1250, and the receiver reservoir 1255. However, the sample holder can be a microscope slide, a "gene array chip", a clamp, or any other device that can hold a sample for analysis. In fact, the sample holder can be the sample itself of part of the sample's environment, if, for example, the sample is a letter in a mail sorting facility, dust on a table surface, or microbes on the leaf of a tree.

This apparatus is "trained" to recognize a specific pathogen such as anthrax spores or smallpox viruses by first placing a sample of the pathogen in the sample holder, irradiating the pathogen by one or more light pulses, and selecting a feature from the fluorescence spectrum emitted by the pathogen in response to the pulses. The pulse shape is varied while the selected spectral feature is observed, and an optimization procedure is followed to find the pulse shape that maximally enhances the selected feature.

For example, control parameters of pulse shape (such as voltages controlling the attenuation and delay of spectral and polarization components of the pulse) may be treated as genes in a genetic algorithm, and the strength or contrast of the selected feature may be treated as fitness in the evolutionary algorithm to evolve a pulse shape that optimally enhances the selected feature. After optimization for a specific pathogen, the control parameters and the selected feature for that specific pathogen are stored in a computer memory.

In order to detect the specific pathogen in an unknown sample, the controller 1217 loads the optimal control parameters into the pulse shaper 1210 which then generates shaped pulses. Those shaped pulses stimulate fluorescent light emission 1234 by the sample. The fluorescence spectrum analyzer 1237 receives the fluorescent light from the sample and analyzes the fluorescent light to determine whether or not the selected feature is present, and its relative intensity. If the pathogen is present in the sample, the selected spectral feature will be detected. If the feature is not detected by the analyzer, either the pathogen is not present or it is present in too low a concentration to produce a detectable signal.

Embodiment #2

A Pulse Shaper with Phase, Amplitude and Polarization Control

Figure 6:
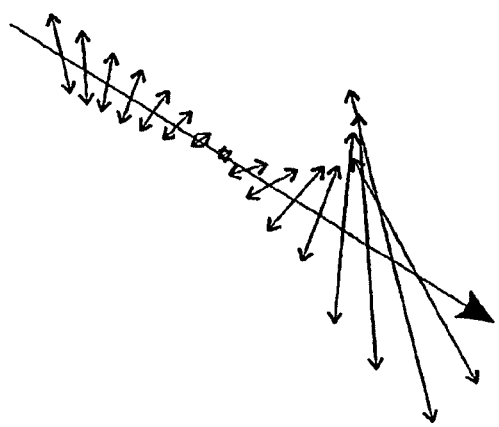
FIG. 6 is a representation of an optical pulse shaped in phase, amplitude and polarization.
Figure 7:
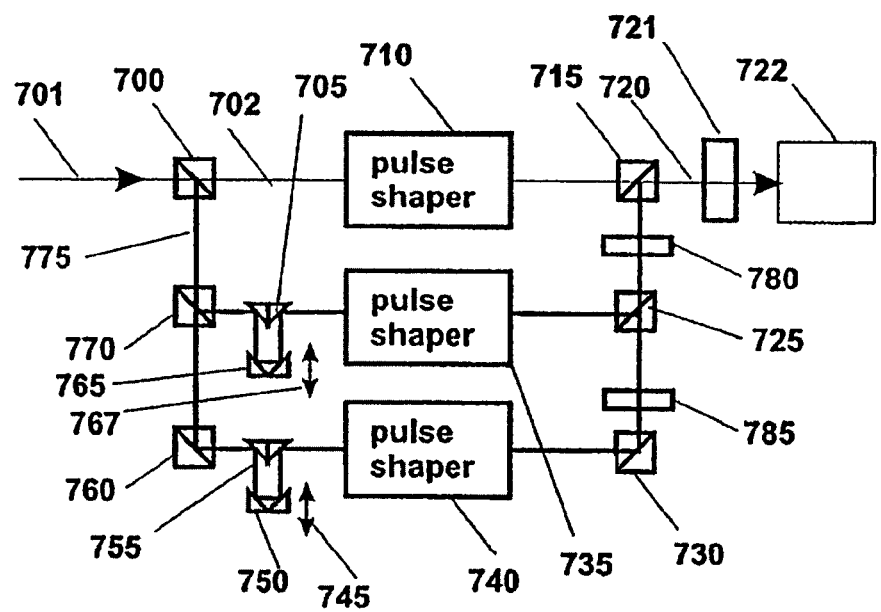
FIG. 7 illustrates a schematic of an apparatus for coherently summing multiple independently shaped pulses with variable delays between them.

The apparatus in FIG. 7 is a pulse shaper for light pulses, on the order of femtoseconds to nanoseconds in duration. An original collimated pulse 701 is split by a polarizing beamsplitter 700 into two pulses 775, 702 with orthogonal polarization. In the path of each pulse, a non-polarization pulse shaper 710, 735, 740 is placed. As shown in FIG. 1, in the non-polarization pulse shapers, a dispersive element 130 such as a diffraction grating or a prism spreads the spectrum of an original light pulse out to a line. The diverging light in the spread spectrum is collimated by a lens 140 or by a curved mirror, then is passed through one or more spatial light modulators 110,105 to adjust the relative phase and amplitude of each spectral component relative to the other components. After passing through the spatial light modulators, the light is focused to a point by a second lens 155 onto a second diffraction grating 100 where it is re-formed into a pulse having only one essentially pure polarization state. As shown in FIG. 7, the pulses emerging from the two pulse shapers 710, 735, still having orthogonal polarizations, are recombined into a single collimated pulse by means of a polarizing beamsplitter 725. By using path length adjuster 765 to adjust the relative phase of the two orthogonal polarization components of each spectral component, any desirable polarization state (e.g., right circular, left circular, linear or elliptical) can be achieved for that component after the two polarization components are recombined. By thus adjusting the relative phase, amplitude and/or polarization state of every spectral component of the recombined pulse, any desired pulse shape can be generated as illustrated in FIG. 6. FIG. 6 illustrates a light pulse whose polarization direction rotates clockwise, then counterclockwise, as its amplitude varies.

Embodiment #3

Scanning Near-field Optical Probe Microscope

Figure 4:
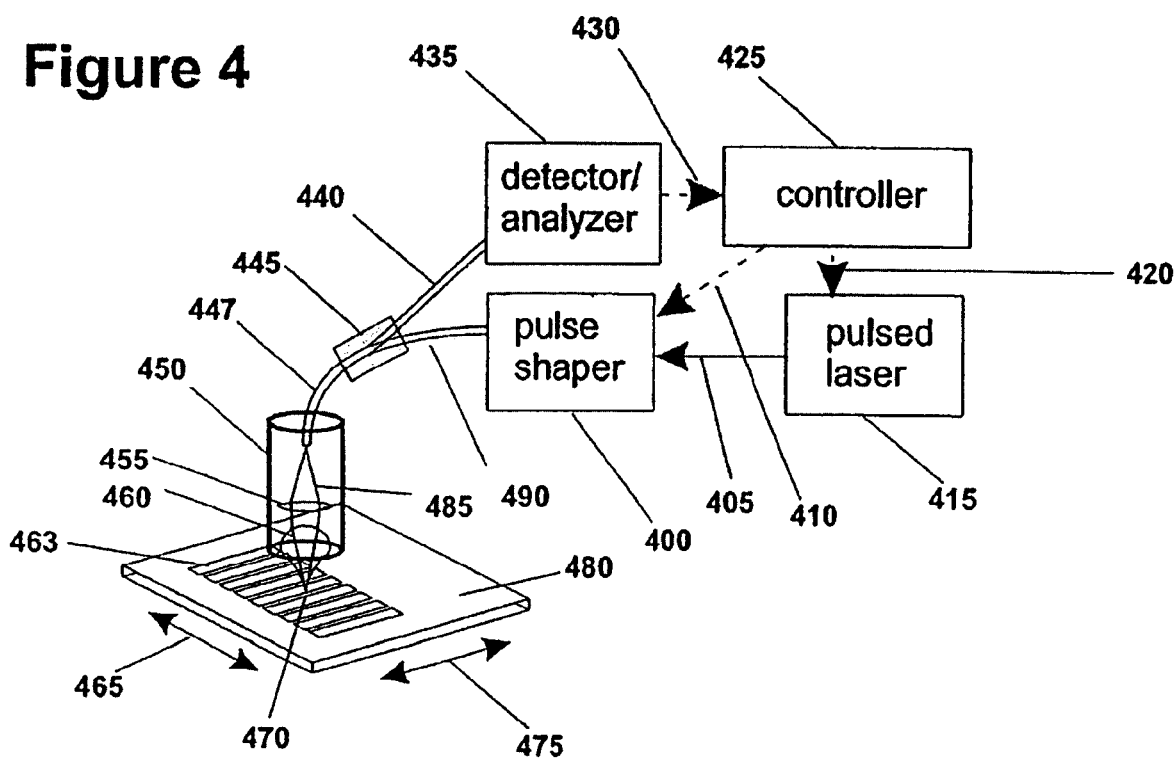
FIG. 4 illustrates a near-field optical scanning microscope using tailored optical pulses for specific substance recognition, including a pulsed laser, a pulse shaper feeding pulses into an optical fiber, a fiber beamsplitter, a near-field probe, and means for moving a sample relative to the probe.

As shown in FIG. 4, a shaped pulse of light may be coupled into an optical fiber 490 and thence into the optics 455, 460 of a near-field scanning optical probe microscope 450. Scattered light from the pulse and fluorescent light stimulated by the pulse may be gathered either by the optical fiber 447 or by other means such as a microscope objective and analyzed with respect to spectrum, polarization and phase by means of a spectrometer or time-resolved spectrometer and other suitable optics 435. Phase analysis requires interfering the gathered light with a portion of the original pulse and examining the position of fringes in the interference pattern. Scattered light may be analyzed for features in the absorption spectrum, while emitted fluorescent light may be analyzed for features in the emission spectrum. Any particular substance at the locus of the evanescent light field from the tip of the microscope probe will be coherently manipulated by a pulse optimally shaped for that substance, so that one or more features in its absorption spectrum or fluorescence spectrum is enhanced.

In order to determine a satisfactory set of features to use in identifying a substance, and an optimal pulse shape to use in order to enhance those features, the pulse shaper 400 is controlled by feedback via a genetic algorithm or other evolutionary algorithm. The detector/analyzer 435 gathers scattered and fluorescent light from the sample. The gathered light may be separated into orthogonally polarized beams, and the spectrum of each beam is digitized and analyzed. Separately, the un-separated beams are passed through a pulse polarization phase shaper as illustrated in FIG. 7 and thence through a linear polarizer, and the phase delay of each spectral component is adjusted until a maximum amount of light is received at a detector 722. The relative phase of the two polarization components at each wavelength, and hence the polarization of each wavelength, may then be expressed for example in terms of the phase delays imposed at that wavelength by each of the two arms of the polarization pulse shaper. The complete configuration of a pulse can then be described in terms of the polarization, phase and amplitude of every spectral component of the pulse. These quantities may be arranged into a complex-valued matrix to represent the pulse. Both the stimulating pulse and the gathered light may be analyzed and represented using the same general matrix form.

A "satisfactory feature" may be defined as the difference between the two matrices describing gathered light when the sample is stimulated with two differently shaped pulses, when the correlation between the two matrices is minimized by selecting different shapes for the two pulses. So, in the genetic algorithm controller, a fitness value is calculated as the correlation between the gathered light resulting from two pulses separated by a time greater than the relaxation time of the sample. The shapes of the two pulses are controlled by the genetic algorithm, to search for two pulse shapes that produce maximally different stimulated signals from the sample.

The scanning near-field optical probe microscope of this embodiment may thereby be trained to recognize specific substances in a sample, with the high spatial resolution typical of scanning probe microscopes. If the microscope is trained to distinguish between individual nucleotides, it may be used to read directly the nucleotide sequence of a DNA molecule.

Embodiment #4

Molecular Scale Data Storage and Retrieval System

If a scanning probe microscope is used to selectively position different types of atoms or molecules at different locations on a surface 480 such as the surface of a silicon crystal or a quartz crystal, such that the arrangement of atom types encodes information, the scanning probe microscope of Embodiment #3 and FIG. 4 may be used to read the information. It is possible to manufacture replicas of such an arrangement of molecules in some cases. For example, if the original is in the form of various protein molecules bound to a surface, a replica may be made by pouring a mixture of antibodies to those protein molecules over the protein molecules. Complementary antibodies will bind to the protein molecules. A coating of silicone rubber, or a UV curable resin coating may then be applied over the antibody layer. After curing, the rubber or resin coating may be peeled off to make an intermaster. Finally, the process can be repeated using proteins or antibodies complementary to the antibodies first coated on the proteins, to make a replica of the original protein arrangement or an equivalent arrangement of antibodies on a resin or rubber surface. This process can be repeated multiple times, subject to the rate of degradation of the master or intermaster. This data storage and retrieval system potentially can store as much as ten terabytes per square centimeter. This technique for replicating arrays of molecules, termed "Hybridization Transfer Printing", is the subject of a co-pending patent application Ser. No. 10/529,834"

Embodiment #5

Molecular Tags and a Reader for Secure Documents, Products or Packages

In this embodiment, specific types of molecules are applied either randomly or in a pattern onto a label, tag or seal. The apparatus of Embodiment #1 or FIG. 4 may be used as a reader to determine the presence or absence of specific molecule types, and the physical arrangement of specific molecule types that are present, in order to judge the validity of the label, tag, or seal or to read information encoded in the selection and/or arrangement of the molecules. This system is analogous to a multicolor barcode system, in that selection of a molecule type is analogous to selection of an ink color, and the physical arrangement of molecule types is analogous to the physical arrangement of ink markings. In fact, this reader may be used to distinguish between different kinds of inks, or inks with different additives; in which case the analogy is closer.

Embodiment #6

CO2 Detector

Because the present methods provide a way to unambiguously detect the presence of any specific type of molecule, the apparatus of FIG. 12 may be used to detect the presence of carbon dioxide or any other potentially harmful gas or vapor in the air or in exhaust emissions. A sample of the air or other gas or vapor to be tested is passed through the tube 1265, or equivalently through an unconfined optical path. A measurement of the quantity or concentration of a specific substance in a sample may be obtained by comparing the intensity of the emitted fluorescent signal to the intensity of the stimulating pulse, at the optimum pulse shape. To obtain a stronger signal by in creasing the path length through the sample volume, the optical path may be folded using mirrors. When the path length over which the shaped pulse interacts with the sample is very long, it is advantageous for the detector 1237 to observe selected features in the absorption spectrum and optimize the pulse shape to enhance those selected features.

Embodiment #7

Cell Sorter

Figure 13:
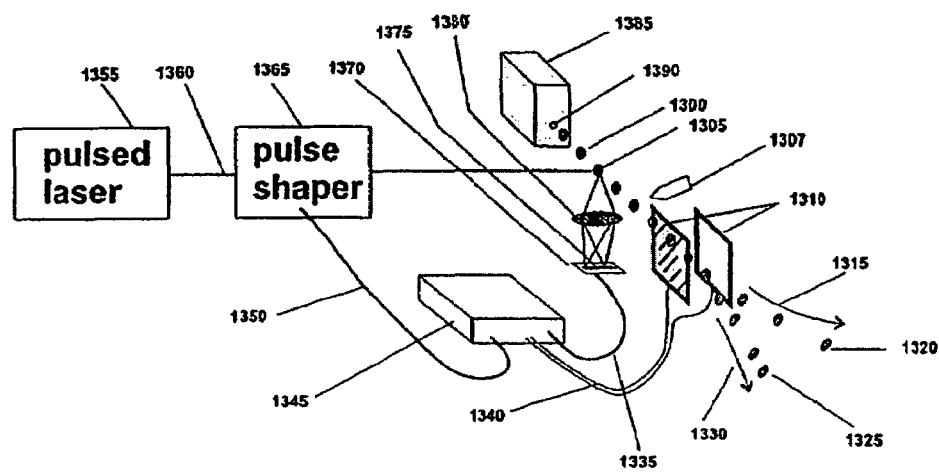
FIG. 13 illustrates an apparatus for sorting particles via shaped pulse identification.
Figure 14:
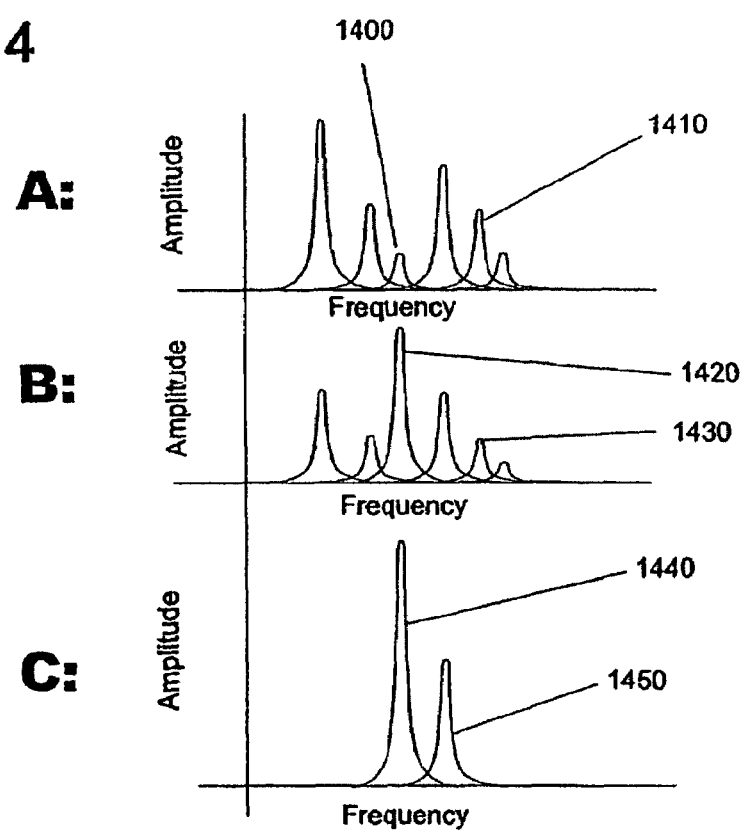
FIG. 14 is an illustration of enhancement of a complex spectral feature by shaped pulse excitation. Part A represents the spectral response of a substance to an unstructured white-light pulse; Part B represents the spectral response of the same substance to an optimally shaped pulse, and Part C represents the difference between normalized versions of the two spectra.

The apparatus of FIG. 13 is capable of detecting and identifying specific kinds of microbes and spores, and it may be used as a cell sorter. A droplet (e.g., 1300) diluted sufficiently that it probably contains a single cell or spore of the type of interest is formed and moved through a focal region 1305. An ink jet printer head 1385, for example, can form and launch droplets of very consistent small size at a high rate. A pulse (from a pulsed laser 1355) shaped by a pulse shaper 1365 to selectively stimulate a specific type of cell or spore illuminates each droplet, and light scattered and emitted by the droplet is gathered by optics 1380, directed onto detector 1370 and analyzed by computer 1345. If desired, filters may be positioned anywhere between focal point 1305 and the detector 1370 to pass only selected parts of the spectrum to the detector; however, if the optical system 1380 employs a prism or diffractive element to spread the spectrum of the light from the sample onto a detector array 1370, it is not necessary to filter the spectrum optically. The computer 1345 may employ an FPGA or other highly parallel signal processor for high speed, or it may be a high speed serial computer. The droplet 1300 may then be charged by ion source 1307 or electron source 1307 and deflected electrostatically by voltages applied to plates 1310 or by gas jets or other deflection means 1310 under the control of computer 1345 into different paths 1315, 1330 according to whether or not a specific type of microbe or spore has been detected in the droplet. This system has applications in directed evolution of microbes, medical diagnostics, and assays of microbial populations.

Embodiment #8

Optical Security Device

An optical security device can be made by applying specific nonlinear optical materials such as fluorescent dyes or specific proteins to a tag or label. In FIG. 4, such a label 480 bears stripes of inks containing fluorescent quantum dots such as ZnSe-capped CdS nanocrystals. Alternatively, markings or taggants 463 may be applied to a surface 480 of a product in the form of a pattern of nonlinear and linear optical materials in a resonant structure such as a multilayered interference filter, or particles of nonlinear optical materials may be incorporated into the volume of the label or surface 480. An appropriately tailored optical pulse illuminating a spot 470 will move the fluorescent particles or nonlinear optical materials or structures into an excited state, which will decay by emitting light and/or phonons. The emitted spectrum or absorption spectrum may be detected and analyzed by detector and computer 435, to identify the markings, materials, particles, patterns or structures and thereby determine the identity or validity of tag, label, document or product 475.

Embodiment #9

Opto-Acoustic Signals Stimulated by Shaped Optical Pulses

Figure 10:
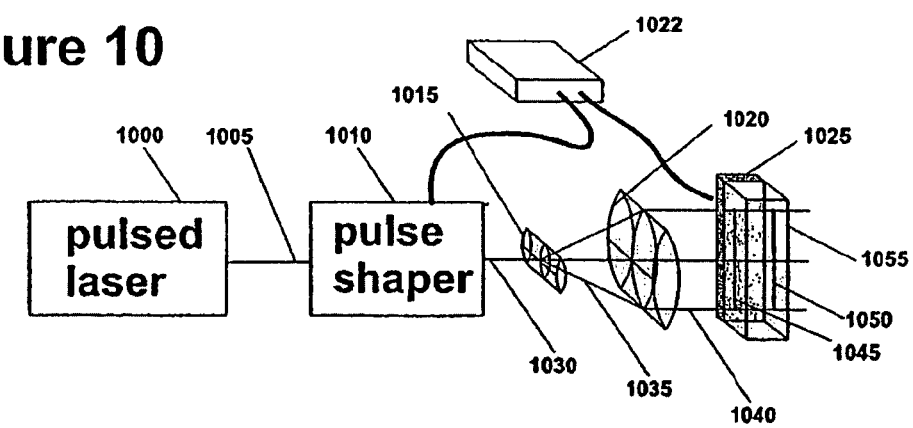
FIG. 10 illustrates an opto-acoustic apparatus including a cuvette, an acoustic transducer, optics to form a thin "sheet" of light, a pulsed laser and a pulse shaper. The pulse shaper can include the ability to shape the polarization of the pulse.

Molecules of a given type in solution will emit a characteristic acoustic pulse when stimulated by an optical pulse. The detailed shape of the acoustic pulse depends on the optical spectrum of the molecules and the details of energy exchange between the molecules in their various states and the surrounding medium. Thus, an optical pulse having the specific shape to place the molecules into a specific excited state will cause the molecules to emit an acoustic pulse having a distinctive shape. In FIG. 10, a shaped optical pulse excites a target molecule type in a cuvette 1055. Acoustic energy emitted by the molecules in response to the pulse is picked up by acoustic transducer 1025 and analyzed by computer 1022.

Embodiment #11

Improved Scanned Probe Near-field Optical Microscope

The response of a molecule to an optical pulse depends on the polarization of the pulse, the orientation of the molecule, the quantum state of the molecule and the atoms composing the molecule, and the phase of the quantum state. Accordingly, it is advantageous to precondition the molecules so that a large fraction of the molecules in a sample are aligned and in a specific quantum state and phase. This preconditioning may be obtained by several methods. One method is to use a relatively long optical pulse tailored in frequency and polarization to align nuclei in the molecules, for example via the Overhauser effect. Another method is to place the sample in a stationary magnetic field modulated by a rotating magnetic field as is standard in NMR technology, to align the molecules or nuclei and synchronize their precessional phases. Another method is to mechanically align molecules by embedding them in a stretchable material and stretching the material. Yet another method is to crystallize the molecules or incorporate them in a crystalline matrix composed of another material.

Figure 8:
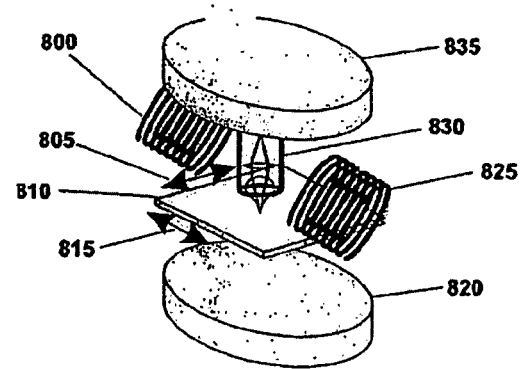
FIG. 8 illustrates an apparatus including a strong static magnet, RF coils, and a near-field probe for combining NMR spectroscopy and scanned optical near-field microscopy with tailored-pulse excitation.

The scanning near-field optical microscope of FIG. 4 may be modified as in FIG. 8 to further enhance the signal from a sample. FIG. 8 illustrates the optical head of FIG. 4, with field magnet poles 820, 835 added, and RF coils 800, 825 added. The quantum state of the target molecules or atoms in a sample on substrate 805 may be pre-conditioned using the magnetic field generated by poles 820, 835 and the RF coils 800, 825 or by the optical Overhauser effect using a preconditioning light pulse of specific frequency and polarization. The pre-conditioned sample may then be probed using one or more further pulses shaped optimally to enhance features in the optical absorption or emission spectrum of the sample. Alternatively or in addition, RF signals picked up by coils 800, 825 may be analyzed to provide information further useful in identifying and detecting the target molecules or atoms in the sample using standard NMR techniques.

All of the embodiments described above may additionally include means to generate multiple coherent pulses with adjustable delays between pulses. FIG. 7 illustrates one such means. An original pulse with, say, a Gaussian shape, is converted to several coherent pulses of nominally identical shape using a train of beamsplitters 700, 770, 760. Additional elements 750, 765 may be inserted in the beam paths to ensure that all pulses experience the same dispersion. Pulse shapers 710, 745, 740 may be inserted in the paths to shape each pulse independently, and then the pulses may be directed into a common beam path using beamsplitters 715, 725, 730. Coherent pulse amplifiers 721 may be inserted into the separate paths or into the common beam path, and attenuators 780, 785 may be inserted to control the relative amplitudes of the different component pulses. By adjusting the length of each path (for example by moving the mirrors 750), the timing between pulses may be adjusted. Multiple, mutually coherent, independently shaped pulses are advantageous because they may be used to prepare a desired quantum state of a molecule and then probe the state. For example, the absorption spectrum of a molecule depends on the state it is in. The first pulse can drive the molecule into a given state, and the absorption spectrum of the molecule relative to the second pulse is then distinctive of the molecule in that state. Furthermore, the absorption cross section of a photon by a molecule depends on the polarization, wavelength and phase of the photon as well as the quantum state of the molecule, so the absorption spectrum measured via the second pulse may depend strongly on the detailed shape of the pulse.

Note that the superposition of two coherent light beams of orthogonal polarization and having slightly different wavelengths results in a rotating electric field vector and a rotating magnetic field vector in the light beams, rotating at a frequency dependent on the frequency difference between the two beams.

Figure 2:
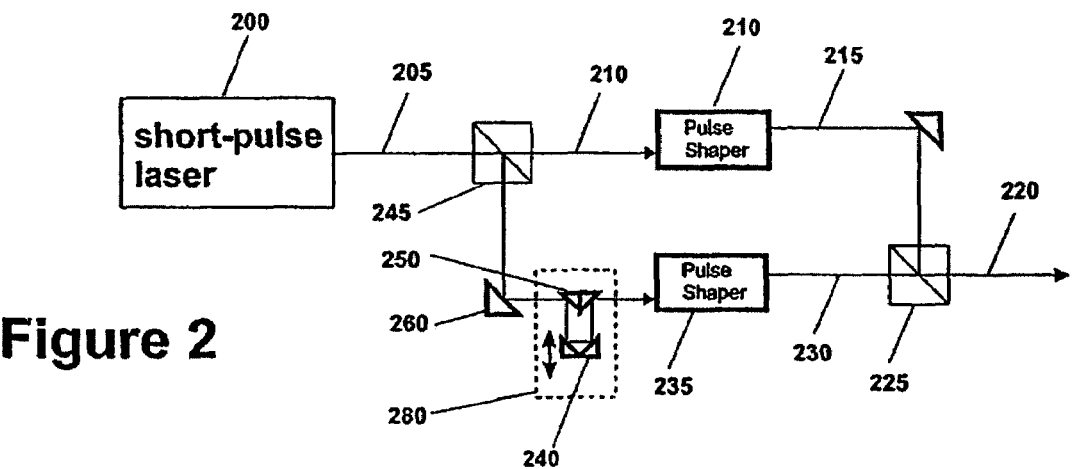
FIG. 2 illustrates an apparatus for shaping femtosecond light pulses adaptively with independent control of polarization, amplitude and phase at multiple wavelengths. The apparatus uses a pair of pulse shapers, one for each of two orthogonal polarization states in separate paths. A variable delay element is included in one of the paths to adjust the relative timing and/or phase of the two polarization states.

Any of the embodiments above may also be implemented with a plurality of re-shaped pulse combined into a single pulse with different shapes in different polarization planes. FIG. 2 illustrates an embodiment where a pulsed beam 205 from a coherent light source 200 is initially split by beam splitter 245 into separate beams 210 and 211 that are independently re-shaped by separate pulse shapers 232 and 235. In a typical embodiment, the beam splitter 245 includes a polarization rotator (see FIG. 15) so that separate beams 210 and 211 are orthogonally polarized with respect to one another. Depending on the arrangement of the pulse shapers 232, and 235 a first mirror 260 can be used to direct one of the beams 211 into at least one of the pulse shapers 235. A path length adjuster 240 can be interposed in the path of at least one of the beams 210 or 211 to assure the separate beams remain in phase. Each of the pulse shapers 232 can be configured with different control parameters to independently re-shape the separate pulses 210, 211 into different pulse shapes 215, 230, which are recombined into a combined pulse 220 by beam combiner 225. The combined pulse 225 thus contains a mixed polarization pulse having different shapes in different planes of polarization.

Embodiment #12

Another Quantum Resonance Controlled Fluorescence Microscope

Because the microscope embodiments disclosed herein can be controlled so as to optimally detect fluorescence or other emissions from discrete substances in a specimen due to quantum resonance effects, each of these embodiments are denoted herein as a "quantum resonance controlled fluorescence" (QRCF) microscope.

Other embodiments of such microscopes can use two polarization-shaped beams intersecting at the object plane of a microscope to illuminate an object such as a living cell or other specimen mounted on a specimen holder. To shape the polarization as well as the other features of a pulse, the pulse is divided into two orthogonally polarized beams using a polarizing beamsplitter. The two beams are shaped independently and then recombined to form a shaped pulse using a system such as described in FIG. 2. In still further embodiments, two such polarization-controlled pulses can be produced, and intersected at a mutual angle of at least 45 degrees, and most preferably at 90 degrees, to illuminate the object in a fluorescence microscope. The two pulses, appropriately controlled and shaped, can produce essentially any conceivable sequence of electric field vectors through the duration of the pulse, within the bandwidth of the pulse.

Figure 15:
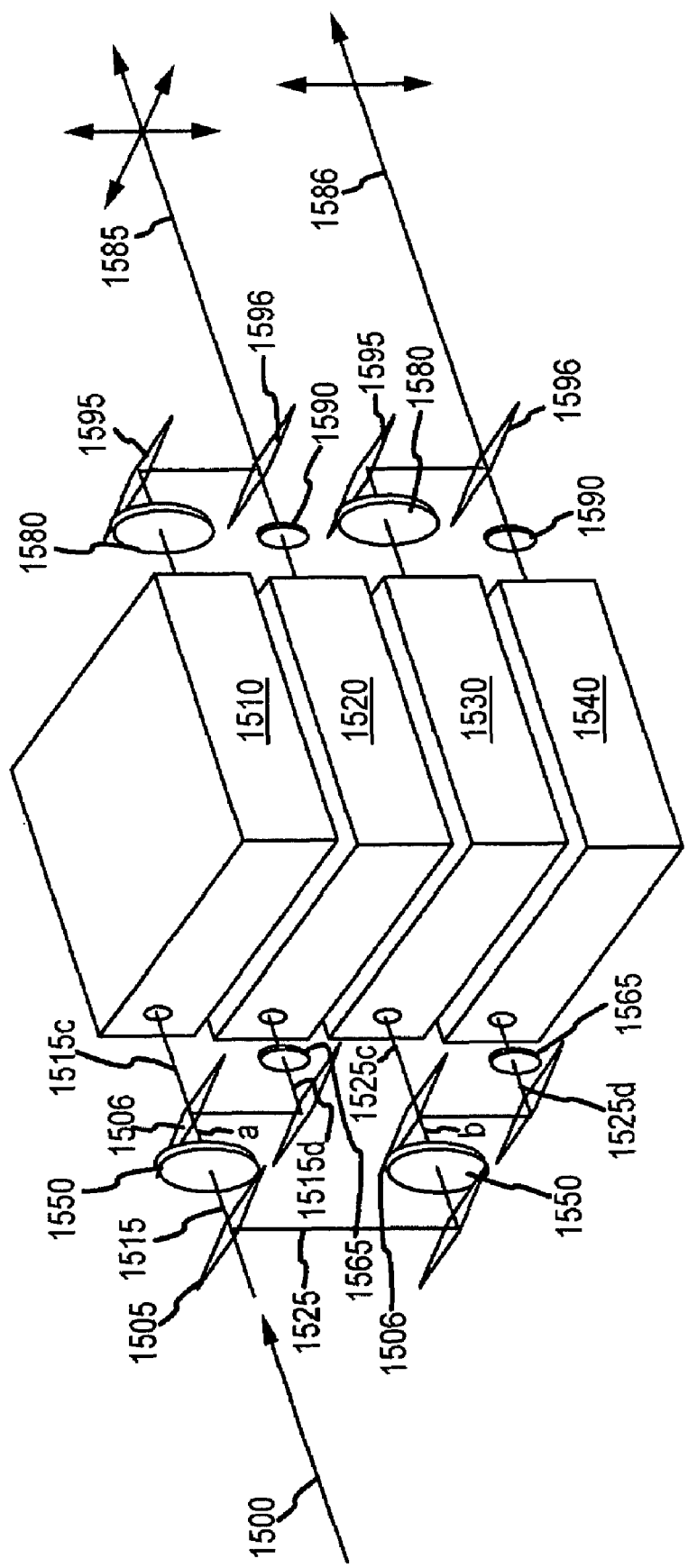
FIG. 15 is an illustration of an apparatus for forming two beams of pulses independently shaped with respect to amplitude, phase and polarization.

In these embodiments, a composite re-shaped pulse having an electrical or magnetic field in each of the X, Y and Z axes is formed by combining pulses independently shaped using additional pulse shapers and beam splitters. While such embodiments are useful in any of the instruments disclosed herein, they are particularly useful in microscope applications for probing a specimen mounted on a specimen holder FIG. 15 depicts an example system for use in an QRCF microscope that uses four identical pulse shaping and recombining modules 1510, 1520, 1530 and 1540 stacked together, one for each polarization component of two separate beams. Three path length adjusters may be included in the modules to ensure that the pulses can be recombined with sub-micron precision. Each pulse shaper module receives a polarized pulse, uses a diffraction grating to disperse the pulse into a spectrum, collimates the dispersed beam, directs the spectrum through a row of pixels in a each of two 2D spatial light modulators, then focuses the beam onto a second diffraction grating to re-form a pulse as previously described. The initial pulse 1500 is first split by a beam splitter 1505 into separate beams 1515 and 1525. Each of these beams is filtered by a first set of polarization rotators 1550 into polarized beams "a" and "b". The polarized beams "a" and "b" are passed through a second set of beam splitters 1506 to produce four beams 1515c, 1515d, 1525c, and 1525d. At least two of these beams are maintained in one plane of polarization, and at least one of the remaining beams is then passed through a second polarization rotator 1565 to rotate that beam's polarization into an orthogonal plane of polarization with respect to the other two. Each of the pulse shapers 1510, 1520, 1530 and 1540 independently re-shape their corresponding incident beams. A second set of polarization filters 1580 and 1590 and mirrors 1595, 1596 act as a pulse combiner to recombine the independently re-shaped pulses into two emergent beams 1585 and 1586. One of the emergent beams 1585 is a superposition of two beams having two different orthogonal planes of polarization to form a mixed polarization beam. The remaining beam 1586 is a linearly polarized beam having one plane of orientation.

While the example depicted in FIG. 15 is illustrated with four pulse shapers, this illustration is solely for the sake of symmetry to indicate that either of the initially split beams 1515a or 1515b by can be re-shaped into either the recombined mixed polarization beam 1585 or the linearly polarized beam 1586. It is understood however, that only three pulse shapers are actually required, two of which emit beams of orthogonal polarization to be recombined into the mixed polarization beam 1585 and the other to emerge as a linearly polarized beam 1585.

The four pulse shaping modules 1510, 1520, 1530 and 1540 depicted in FIG. 15 are stacked so that they can all use separate rows of a single pair of spatial light modulators within each pulse shaper, although in alternative embodiments the four modules can be physically separate The modules can be built from off-the-shelf components such as dielectric mirrors, polarization beamsplitters and adjustable mounts. In one exemplary embodiment, the system will use a CRL Optics SLM model for the pulse shaping. This SLM is an "analog" device as opposed to a "time division" device. Whereas pixels in the "time division" device produce gray scale modulation by turning fully on and fully off for various portions of each frame cycle, pixels in the "analog" device only turn partly on for the full duration of each frame cycle. When a short light pulse passes through a "time division" SLM pixel, it can only be turned "on" or "off" by the pixel, depending on the relative timing of the pulse and the frame cycle. A pulse passing through an "analog"SLM pixel is modulated to the same degree regardless of its timing relative to the frame cycle.

The two re-shaped pulses 1585 and 1586 emergent from the pulse shaping modules preferably arrive at the object in the microscope at the same instant, with variations not exceeding a few tenths of a femtosecond. One femtosecond corresponds to about a third of a micron, so the path lengths of the beams should be adjustable to about a tenth of a micron. The pulse shaping modules 1510, 1520, 1530 and 1540 can, for example, include appropriate path length adjusters to accomplish this purpose as described herein above.

Each pulse shaper assembly needs be interferometrically stable (i.e., within a variance substantially less than one wave length, for example less than $1/10^{th}$ or $1/20^{th}$ of the wavelength of radiation used. Although there is essentially no possibility of motion during a pulse, it is important for all components to remain in the same relative positions over relatively long periods of time between pulses, because the adaptive pulse shaping process may depend on coherent superposition of literally hundreds of separate beamlets traveling on different paths. That degree of stability is maintained as a matter of course in systems known in the art, for example, in holographic systems provided by New Light Industries, (Spokane, Wash.). Interferometric stability may be accomplished in many ways. For example, in certain embodiments, the pulse shaping and recombining system can be machined into a single block of metal and surrounded by a temperature-stabilized enclosure mounted on a vibration isolation table to prevent dimensional changes.

Figure 16:
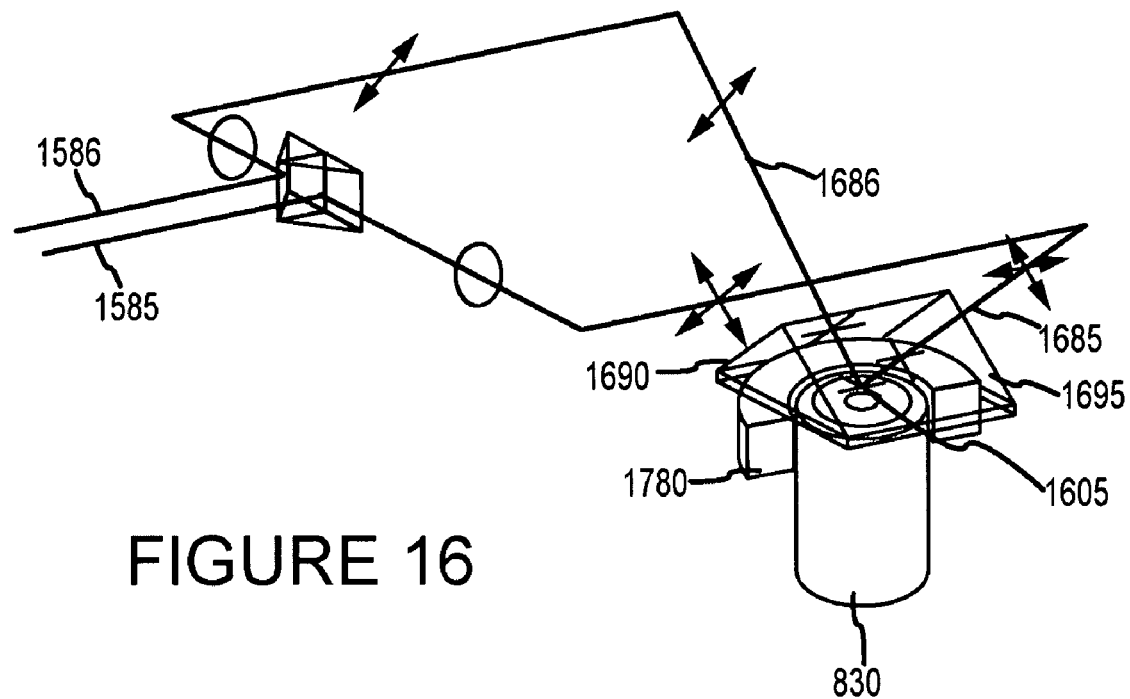
FIG. 16 is an illustration of one possible set of beam paths and optics for combining two independently shaped pulses on a sample in such a way that the direction and amplitude of the electric field vector in the composite pulse is controlled in three dimensions at the sample.

The microscopes used in various embodiments can be either standard or inverted. In some embodiments, an inverted microscope is desirable because its configuration gives easy access to the back side of the specimen and make possible the use of "total internal reflection" illumination as illustrated in FIG. 16. One beam 1686 (corresponding to beam 1586 of FIG. 15) is linearly polarized, carrying a shaped pulse, while the other beam 1685 (corresponding to beam 1585 of FIG. 15) is a superposition of two shaped pulses polarized orthogonally. To avoid interference and reflectance caused by impinging a flat side at an incident angle less than 90 degrees, the flat bottom of an antireflection coated prism 1690 can be used as the specimen mount while each of beams 1685 and 1686 enter the prism at a 90 degree angle to the side surfaces 1685 of the prism. At a point 1605 at the bottom of the prism 1690 the two beams intersect on the specimen at a mutual angle of at least 45 degrees, and preferably at 90 degrees so the electric field axes of the three pulses are all mutually orthogonal in an X, Y, Z coordinate system. Thereby, complete three-dimensional control of the electric field vector in the object illumination is possible on a femtosecond timescale. FIG. 16, like FIG. 8, further shows a magnetic coil 1780 (and/or RF source not shown) configured to orient molecules within the specimen as well as a microscope objective lens assembly 830 that will image the emitted radiation received from the specimen as a result of being stimulated by the pulses in the combined beams. Color-selective filters may be employed to image only light of selected wavelengths.

Figure 17:
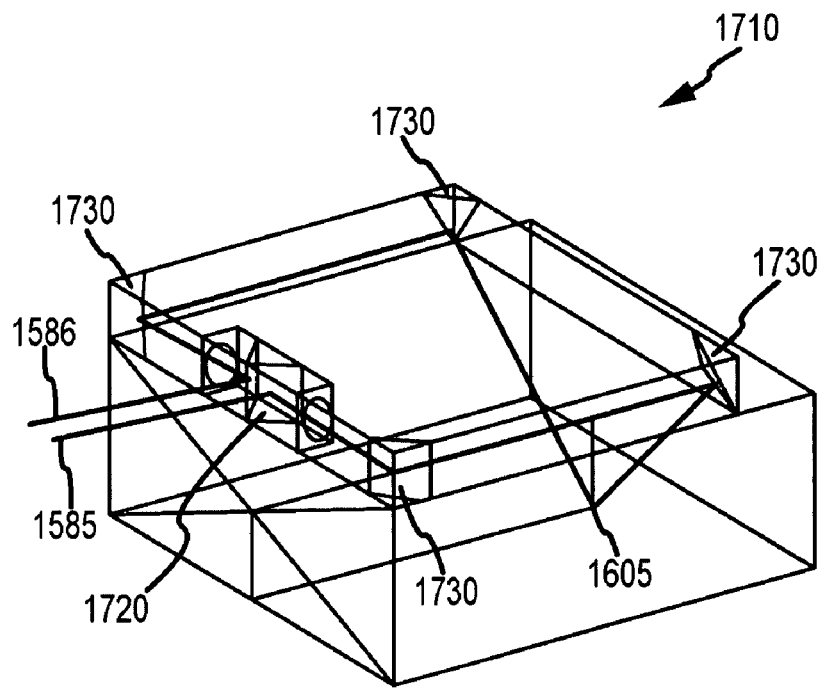
FIG. 17 depicts a glass block embodiment configured to provide the beam paths illustrated in FIG. 16.

As depicted in FIG. 17, instead of using the prism 1690, in certain embodiments, the beams can be totally internally reflected at the bottom face of a solid block 1710 using appropriate mirrors 1720, 1730 or coatings so the specimen on the bottom face of the prism will be illuminated solely by the evanescent field of the reflected light, extending about a quarter of a micron from the prism face at the point of intersection 1605. All of the beam recombiner optics can thus be incorporated into a solid block of glass as illustrated in FIG. 17 to ensure stability. The specimen holder can be located directly beneath the single block of glass, or in alternative embodiments, the bottom of the single block of glass 1710 can itself serve as the specimen holder.

Anticipated advantages of the methods and apparatus provided herein include a) the ability to identify the presence and distribution of specific molecular species in living cells, b) the ability to characterize interactions between specific molecular species and their intracellular environment, c) the ability to image distributions of nonradioactive isotopes in a specimen, and d) the prospect of highly selective triggering of specific chemical reactions at selected locations in a living cell. By adjusting the voltage on each element of the SLM of the pulse shapers, the pulse can be modified in almost any conceivable way. By splitting the pulse into two parts, shaping the parts independently, rotating the polarization of one and recombining the two, the time-dependent polarization of the resulting pulses can be shaped as well.

The time-dependent frequency and polarization of a light pulse can be tailored to induce quantum state transitions that would be extremely unlikely under simple pulsed illumination of a substance. As a result, a properly tailored pulse shape can induce fluorescence selectively in specific molecular species and at specific wavelengths. Both the pulse shape and the resulting emission spectrum are thus specific to one and only one molecular species. When optimized for the detection of one particular type of molecular substance in the specimen, the QRCF microscopes provided herein are able to reveal the spatial distribution of the substance throughout a cell, by causing only molecules of that type to fluoresce. Variations in the tuning should reveal spatial variations in the state of the molecules resulting from folding, weak bonding, dissolved ion concentrations, and so on. When tuned to each of a series of different molecules in turn, the QRCF microscope should be able to build up a detailed micron-scale picture of the molecular composition and structure of a cell.

Specific elements and combinations of elements of the embodiments and techniques described herein may be changed without departing from the scope of the invention as long as the essential principles are followed. For example, microwave radiation or acoustic radiation may be substituted for light radiation if the pulse shaper is of a type suitable for shaping microwave or acoustic pulses respectively. Fiber optic beamsplitters instead of cube beamsplitters may be used for splitting and combining pulses. A polarization pulse shaper may act upon any orthogonal polarization components of a pulse such as orthogonal linear polarizations, orthogonal circular polarizations or orthogonal elliptical polarizations. The pulses may be of any suitable duration including femtoseconds, picoseconds, nanoseconds, microseconds or milliseconds depending on the quantum state structure of the target particles or substances. In addition, the radiation emitted from the component substance being detected is not limited to fluorescent emission, but may include differential absorbption, -upconverted light, X-ray, UV, visible, IR, terahertz, RF, or acoustic radiation. Upconverted light is light emitted at a shorter wavelength than the wavelength of the stimulating light.

The shaped pulses made by the polarization pulse shaper may be used in any application in which it is beneficial to tailor the polarization shape as well as the phase and amplitude shape of a pulse, such as in controlling chemical reactions, separating isotopes, inducing optical transparency, preparing specific quantum states for a quantum computer, or enhancing the ability of a light pulse to damage a target.

The term, "substance" as used herein, means particles, cells, spores, molecules, atoms, crystalline structures, quantum dots, or nanocrystals having consistent optical properties and emission or absorption spectra that depend on the shape of a stimulating coherent radiation pulse. The term, "particle" is used to refer to any object smaller than approximately 50 microns in diameter, including cells, spores, pellets. The particles may themselves be composed of substances that are detected or recognized by the apparatus as described herein, or they may be tagged or marked with such substances.

The term "focus" is used herein to mean "bring to a point"; and it is also used to mean "form an image".

The invention claimed is:

1. A microscope system for detecting a distribution of a component substance in a specimen, comprising:
   a pulse shaper configured to re-shape an initial pulse of radiation emitted from a radiation source;
   an illuminating assembly configured to illuminate the specimen with the re-shaped pulse; and
   objective optics configured to focus radiation emitted from the specimen when the specimen is illuminated with the re-shaped pulse into an image representing a distribution of the component substance in the specimen.

2. The microscope of claim 1 wherein the initial radiation pulse is re-shaped to modify at least one of phase, amplitude and polarization of at least one spectral component of the initial radiation pulse.

3. The microscope of claim 1 further including a detector that detects the focused radiation emitted from the component substance of the specimen.

4. The microscope of claim 1 wherein the radiation source is from a femtosecond laser that provides coherent radiation pulses of consistent initial shape and duration.

5. The microscope of claim 1 wherein the pulse shaper is configured to re-shape at least one of phase, amplitude and polarization of at least one spectral component of the initial radiation pulse and further including a controller configured with control parameter sets that cause the pulse shaper to re-shape the initial pulse into at least one differently shaped pulse and wherein each set in the library is optimized to cause a distinguishable radiation signature to be emitted from a different target substance component of the specimen.

6. A microscope for detecting a distribution of a component substance in a specimen, comprising:
   a plurality of pulse shapers configured to re-shape an initial pulse of radiation emitted from a radiation source into a first re-shaped pulse that is linearly polarized, and a second re-shaped pulse that has combined polarization;
   an illuminating assembly configured to simultaneously illuminate the specimen with the first and second re-shaped pulses so that the first and second re-shaped pulses intersect at an angle of at least 45 degrees on the specimen to form a combined pulse having at least three mutually orthogonal electric fields; and
   objective optics configured to focus radiation emitted from the specimen when the specimen is illuminated with the re-shaped pulses into an image representing a distribution of the component substance in the specimen.

7. The microscope of claim 6 wherein the first and second re-shaped pulses intersect at an angle of about 90 degrees.

8. The microscope of claim 6 wherein the illuminating assembly is comprised of a totally internally reflective device and the first and second re-shaped pulses are guided within the internally reflective device to intersect at the angle of at least 45 degrees.

9. The microscope of claim 6 wherein the specimen is mounted on or beneath a horizontal surface of a prism and the first and second re-shaped pulses enter the prism through first and second surfaces orthogonal to the horizontal surface.

10. The microscope of claim 6 wherein the each of pulse shapers is configured to re-shape at least one of phase, amplitude and polarization of at least one spectral component of the initial radiation pulse and further including a controller configured with control parameter sets that cause the pulse shapers to independently re-shape the first and second pulses emitted into different re-shaped pulses; wherein the control parameters sets are selected from a library, each set in the library being optimized to cause emission of a distinguishable radiation signature from a different substance component of the specimen.

11. The microscope of claim 10 wherein the control parameters in the library are obtained using an evolutionary algorithm comprising:
   a) independently impinging the specimen with a plurality of different re-shaped pulses formed according to a plurality of different sets of control parameters;
   b) independently measuring features of a first spectrum of radiation emitted or absorbed by a target component substance of the specimen when impinged by each the plurality of the different re-shaped pulses and independently measuring the same features for a second spectrum emitted or absorbed from a non target component substance;
   c) determining a fitness value for each of the plurality of control parameters by independently calculating a difference between the measured features of the first spectrum and the second spectrum and assigning the fitness value for each of the plurality of control parameters based on the magnitude of calculated difference;
   d) selecting at least two sets of control parameters that have a higher fitness value than non-selected control parameters;
   e) generating offspring parameter sets from the at least two selected sets of control parameters by randomly substituting at least one parameter from one of the selected sets with at least one corresponding parameter from another of the selected sets;
   f) optionally, mutating the offspring sets by randomly changing at least one parameter of the offspring parameter sets;
   g) repeating acts a-f using the offspring parameter sets or optionally mutated parameter sets to generate the plurality of different re-shaped pulses in act "a";
   repeating act g until a final offspring parameter set is generated that forms a re-shaped pulse that when impinged on the specimen, produces a signature spectrum of radiation emitted or absorbed by the target component substance that is more distinguishable from the second spectrum of radiation emitted from the non-target substances than the first spectrum of radiation emitted; and
   including the final offspring parameter set within the library of parameter sets.

12. A microscope system for detecting a distribution of a component substance in a specimen, comprising:
   a pulse shaper configured to re-shape an initial pulse of radiation emitted from a radiation source into a plurality of pulses each of predetermined shape;
   an illuminating assembly configured to illuminate the specimen with the plurality of pulses; and
   image forming apparatus to receive radiation emitted from the specimen as a result of illumination by the plurality of pulses, and form from the emitted radiation an image representing a distribution of the component substance in the specimen based on the spectral composition of the emitted radiation.

13. The microscope of claim 12 wherein at least one of the plurality of pulses is shaped by modifying at least one of phase, amplitude and polarization of at least one spectral component of the initial radiation pulse.

14. The microscope of claim 13 wherein the emitted light includes at least one of fluorescence, Stokes emission, anti-Stokes emission, upconverted light, Rayleigh scattered light, and Raman scattered light.

15. The microscope of claim 12 wherein the radiation source is from a femtosecond laser that provides coherent radiation pulses of consistent initial shape and duration.

16. The microscope of claim 13 further including a source of time-varying electromagnetic field to configured with the microscope to apply a time-varying electromagnetic field to the specimen to orient via magnetic resonance at least a portion of the component substance of the specimen.

17. The microscope of claim 13 wherein the pulse shaper is configured to re-shape at least one of phase, amplitude and polarization of at least one spectral component of the initial radiation pulse and further including a controller configured with control parameter sets that at least partly determine the shapes of the plurality of pulses.

18. The microscope of claim 17 wherein the control parameters sets are selected from a library, each set in the library being optimized to cause a distinguishable radiation signature to be emitted from a predetermined target substance component of the specimen.

19. The microscope of claim 18 wherein the control parameters in the library are obtained using an evolutionary algorithm comprising:
  a) independently impinging the specimen with a plurality of different re-shaped pulses formed according to a plurality of different sets of control parameters;
  b) independently measuring features of a first spectrum of radiation emitted or absorbed by a target component substance of the specimen when impinged by each the plurality of the different re-shaped pulses and independently measuring the same features for a second spectrum emitted or absorbed from a non target component substance;
  c) determining a fitness value for each of the plurality of control parameters by independently calculating a difference between the measured features of the first spectrum and the second spectrum and assigning the fitness value for each of the plurality of control parameters based on the magnitude of calculated difference;
  d) selecting at least two sets of control parameters that have a higher fitness value than non-selected control parameters;
  e) generating offspring parameter sets from the at least two selected sets of control parameters by randomly substituting at least one parameter from one of the selected sets with at least one corresponding parameter from another of the selected sets;
  f) optionally, mutating the offspring sets by randomly changing at least one parameter of the offspring parameter sets;
  g) repeating acts a-f using the offspring parameter sets or optionally mutated parameter sets to generate the plurality of different re-shaped pulses in act "a";

repeating act g until a final offspring parameter set is generated that forms a re-shaped pulse that when impinged on the specimen, produces a signature spectrum of radiation emitted or absorbed by the target component substance that is more distinguishable from the second spectrum of radiation emitted from the non-target substances than the first spectrum of radiation emitted; and including the final offspring parameter set within the library of parameter sets.

20. The microscope of claim 19 further comprising:

a plurality of pulse shapers configured to re-shape an initial pulse of radiation emitted from a radiation source into a plurality of pulses having controlled amplitude, phase and polarization shapes;

an illuminating assembly configured to simultaneously illuminate the specimen with a subset of the plurality of pulses from a plurality of directions and thereby subject the specimen to an optical field having controlled time-varying amplitude, phase and electric field direction; and image forming apparatus to receive radiation emitted from the specimen subsequent to illumination by the plurality of pulses and to form an image representing a distribution of a component substance in the specimen on the basis of one or more of the spectral composition and the temporal variation of the emitted radiation.

* * * * *

UNITED STATES PATENT AND TRADEMARK OFFICE
CERTIFICATE OF CORRECTION

PATENT NO.         : 7,352,469 B2
APPLICATION NO.    : 11/041005
DATED              : April 1, 2008
INVENTOR(S)        : Stephen P. McGrew It is certified that error appears in the above-identified patent and that said Letters Patent is hereby corrected as shown below:

Title Page; item (56);

| | Reads | Should Read |
|---|---|---|
| 1st Page: U.S. Patent Documents (1st Col.) | "…Trebino et al." | --…Trebino et al. ……356/450-- |
| | "…Mourou et al." | --…Mourou et al. ……372/25-- |
| 1st Page: U.S. Patent Documents (2nd Col.) | "…Eggleton et al." | --…Eggleton et al. …..385/122-- |
| | "…Kane" | --…Kane …………356/450-- |
| | "…Naganuma" | --…Naganuma ……..356/450-- |
| 2nd Page: U.S. Patent Documents (2nd Col.) | "…Rabitz et al." | --…Rabitz et al. …….702/23-- |
| Column 7, Line 21 | "sample itself of" | --sample itself or-- |
| Column 8, Line 45 | "at the locus of" | --at the focus of-- |
| Column 10, Line 28 | "by in creasing the" | --by increasing the-- |

UNITED STATES PATENT AND TRADEMARK OFFICE
CERTIFICATE OF CORRECTION

PATENT NO. : 7,352,469 B2
APPLICATION NO. : 11/041005
DATED : April 1, 2008
INVENTOR(S) : Stephen P. McGrew It is certified that error appears in the above-identified patent and that said Letters Patent is hereby corrected as shown below:

| | | |
|---|---|---|
| Column 10, Line 60 | "ion source 1307 or electron source 1307" | --ion or electron source 1307-- |
| Column 10, Lines 61-62 | "plates 1310 or . . .deflection means 1310 under" | --plates 1310 or . . . . . .deflection means under-- |
| Column 13, Line 4 | "separate pulses 210, 211" | --separate pulsed beams 210, 211-- |
| Column 13, Lines 5-6 | "combined pulse 220" | --combined pulsed beam 220-- |
| Column 13, Lines 6-7 | "combined pulse 225" | --combined pulsed beam 220-- |
| Column 13, Line 44 | "holder FIG. 15" | --holder. FIG. 15-- |
| Column 13, Line 53 | "pixels in a each" | --pixels in each-- |
| Column 14, Line 24 | "physically separate. The" | --physically separate. The-- |
| Column 14, Line 37 | "through an "analog"SLM" | --through an "analog" SLM-- |

UNITED STATES PATENT AND TRADEMARK OFFICE
CERTIFICATE OF CORRECTION

PATENT NO. : 7,352,469 B2
APPLICATION NO. : 11/041005
DATED : April 1, 2008
INVENTOR(S) : Stephen P. McGrew It is certified that error appears in the above-identified patent and that said Letters Patent is hereby corrected as shown below:

| | | |
|---|---|---|
| Column 14, Line 50 | "assembly needs be" | --assembly needs to be-- |
| Column 14, Line 52 | "wave length," | --wave length),-- |
| Column 15, Line 15 | "side surfaces 1685" | --side surfaces 1690, 1695-- |
| Column 16, Line 27 | "absorbption, - upconverted" | --absorption, upconverted-- |
| Column 17, Line 66 | "impinged by each the | --impinged by each of the-- |
| Column 20, Line 16 | "The microscope of claim 19" | --The microscope of claim 12-- |

Signed and Sealed this

Twentieth Day of January, 2009

JON W. DUDAS
*Director of the United States Patent and Trademark Office*